United States Patent
Kropf et al.

(10) Patent No.: US 10,988,710 B2
(45) Date of Patent: *Apr. 27, 2021

(54) ANIONIC SURFACTANTS AND DETERGENTS COMPRISING THEM

(71) Applicants: Henkel AG & Co. KGaA, Duesseldorf (DE); Studiengesellschaft Kohlm mbH, Muelheim an der Ruhr (DE)

(72) Inventors: Christian Kropf, Hilden (DE); Alexander Schulz, Essen (DE); Hendrik Hellmuth, Darmstadt (DE); Roberto Rinaldi, Muehleim an der Ruhr (DE); Hebert Jesus Estevez Rivera, Bochum (DE)

(73) Assignees: Henkel AG & Co. KGaA, Duesseldorf (DE); Studiengesellschaft Kohle mbH, Muelheim an der Ruhr (DE)

(*) Notice: Subject to any disclaimer, the term of this patent is extended or adjusted under 35 U.S.C. 154(b) by 100 days.

This patent is subject to a terminal disclaimer.

(21) Appl. No.: 15/887,611

(22) Filed: Feb. 2, 2018

(65) Prior Publication Data

US 2018/0155654 A1 Jun. 7, 2018

Related U.S. Application Data

(63) Continuation of application No. PCT/EP2016/066577, filed on Jul. 13, 2016.

(30) Foreign Application Priority Data

Aug. 3, 2015 (DE) .................. 10 2015 009 832.2

(51) Int. Cl.
| | | |
|---|---|---|
| C11D 1/00 | (2006.01) | |
| C11D 1/22 | (2006.01) | |
| C07C 305/18 | (2006.01) | |
| C07C 41/09 | (2006.01) | |
| C07C 303/24 | (2006.01) | |
| C11D 17/04 | (2006.01) | |

(52) U.S. Cl.
CPC ............. C11D 1/22 (2013.01); C07C 41/09 (2013.01); C07C 303/24 (2013.01); C07C 305/18 (2013.01); C11D 17/042 (2013.01)

(58) Field of Classification Search
None
See application file for complete search history.

(56) References Cited

U.S. PATENT DOCUMENTS

| 4,138,425 A | 2/1979 | Khodzhakhanov et al. |
| 2006/0079542 A1* | 4/2006 | Nestor .................... A61P 9/04 514/269 |

FOREIGN PATENT DOCUMENTS

| WO | 2008031032 A2 | 3/2008 |
| WO | 2014117973 A1 | 8/2014 |

OTHER PUBLICATIONS

Ferrini, Paola, et al. "Catalytic Biorefining of Plant Biomass to Non-Pyrolytic Lignin Bio-Oil and Carbohydrates through Hydrogen Transfer Reactions." Angewandte Chemie International Ed., vol. 53, 2014, pp. 8634-8639. DOI: 10.1002/anie.201403747.
PCT International Search Report PCT/EP2016/066577 Completed: Sep. 21, 2016; dated Nov. 21, 2016 4 pages.

* cited by examiner

*Primary Examiner* — Necholus Ogden, Jr.
(74) *Attorney, Agent, or Firm* — Thomas G. Krivulka

(57) ABSTRACT

Surfactants of the general formula (I) in which $R^1$ is a linear or branched akyl radical having 6 to 20, especially 10 to 16 C atoms, $R^2$ and $R^3$ independently of one another are H or $H_3CO$, and M is hydrogen, an alkali metal or a moiety $N^+R^4R^5R^6$, in which $R^4$, $R^5$ and $R^6$ independently of one another are hydrogen, an alkyl group having 1 to 6 C atoms or a hydroxyalkyl group having 2 to 6 C atoms, are readily incorporated into laundry detergents or cleaning products, possess outstanding performance qualities and can be prepared on the basis of renewable raw materials.

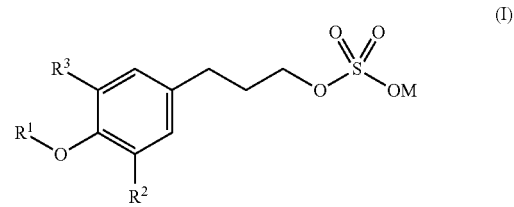

18 Claims, No Drawings

ANIONIC SURFACTANTS AND DETERGENTS COMPRISING THEM

FIELD OF THE INVENTION

The invention relates to anionic surfactants that can be produced based on renewable resources and that comprise low critical micelle concentrations (CMC) and generate low interfacial tensions. The invention also relates to a method for producing such surfactants and washing or cleaning agents comprising these surfactants.

BACKGROUND OF THE INVENTION

The use of surfactants for lowering the surface tension of water, for forming dispersions, and for solubilization has been known, in general, for quite some time in the field of washing and cleaning agents. While a large number of surfactants are produced entirely or partially based on renewable resources, some powerful, widely used representatives are still petrochemically based. Additionally, there is a constant desire to provide surfactants that have outstanding application-related properties so as to be able to achieve high performance, even when using little surfactant.

BRIEF SUMMARY OF THE INVENTION

It is the object of the present invention to provide surfactants that exhibit advantageous application-related properties, such as a low CMC and low surface tension, and that can be produced based on renewable resources. Moreover, the surfactants should exhibit good skin compatibility, and it should also be possible to formulate these together with other surfactants, so as to be suitable, in particular, for use in washing and cleaning agents.

In a first embodiment, the present invention relates to an anionic surfactant of general formula (I),

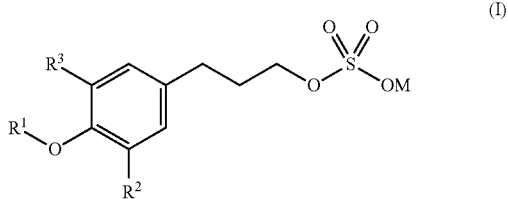

(I)

in which $R^1$ denotes a linear or branched alkyl functional group having 6 to 20, and in particular 10 to 16 carbon atoms, $R^2$ and $R^3$, independently of one another, denote H or $H_3CO$, and M denotes hydrogen, an alkali metal or an $N^+R^4R^5R^6$ grouping, in which $R^4$, $R^5$ and $R^6$, independently of one another, denote hydrogen, an alkyl group having 1 to 6 carbon atoms or a hydroxyalkyl group having 2 to 6 carbon atoms.

Surfactants of general formula (I) can be produced by sulfating a compound of general formula (II),

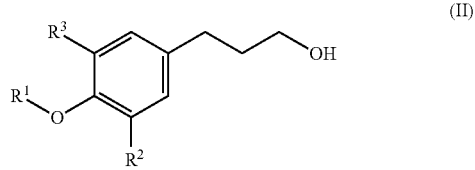

(II)

in which $R^1$, $R^2$ and $R^3$ have the meanings indicated above, with a sulfating agent, such as chlorosulfonic acid, and optionally neutralization by way of subsequent reaction with MOH, wherein M denotes an alkali metal or an $N^+R^4R^5R^6$ grouping, in which $R^4$, $R^5$ and $R^6$ have the meanings indicated above. The invention furthermore relates to such a production method.

The invention moreover relates to a method for producing a compound of general formula (II) by reacting a compound of general formula (III),

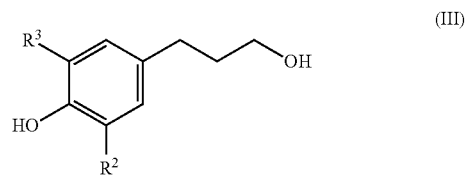

(III)

in which $R^2$ and $R^3$ have the meanings indicated above, with a compound $R^1$-Hal, in which $R^1$ has the meaning indicated above, and Hal denotes chlorine, bromine, iodine or mixtures thereof, and in particular bromine, under alkaline conditions.

The compounds of general formula (III) are 4-(3-hydroxypropyl)-guaiacol, 2-methoxy-4-(3-hydroxypropyl)-guaiacol and 4-(3-hydroxypropyl)-phenol. As described in Angew. Chem. Int. Ed. 2014, 53, pages 8634 to 8639, these can be obtained from wood by way of catalytic biorefinery. 4-(3-hydroxypropyl)-guaiacol can be isolated as the main component from the phenolic components created during the catalytic reaction of wood. In the case of spruce wood, the yield ranges between 5 wt. % and 9 wt. %, based on the wood used. 2-methoxy-4-(3-hydroxypropyl)-guaiacol and 4-(3-hydroxypropyl)-phenol can likewise be isolated in good yields from the phenolic components created during the catalytic reaction of wood. In the case of poplar, the yield of 2-methoxy-4-(3-hydroxypropyl)-guaiacol ranges between 2 wt. % and 5 wt., based on the wood used, and for grasses the yield of 4-(3-hydroxypropyl)-phenol ranges between 2 wt. % and 5 wt. %, based on the grass used.

The surfactants according to the invention have very low CMC values and result in very low interfacial tensions with respect to oil, exhibiting fast dynamics in terms of the organization at the interface. Particularly preferred surfactants according to the invention, in water at a pH of 8.5 and 25° C., have a CMC of 0.005 g/l/ to 0.2 g/l and, at a concentration of 1 g/l/ in water at a pH of 8.5 and 25° C., generate interfacial tension of no more than 2.5 mN/m, determinable by way of the spinning drop method (20-minute equilibration time) against triolein.

The surfactants according to the invention can be obtained from renewable resources as described. Additionally, they have the advantage that the renewable resources from which they can be derived do not form the basis for producing food, so that a situation in which these compete with foodstuffs, as found with some other renewable resources, does not exist here.

The surfactants according to the invention are preferably produced by heating a compound of general formula (III), and in particular 4-(3-hydroxypropyl)-guaiacol, and an alkyl halide $R^1$-Hal in molar ratios up to 1:1, and in particular of 1:1.1 to 1:2.5, in a suitable solvent, such as acetone, and in the presence of a base, such as potassium carbonate, for example heating in acetone under reflux. For purification, the reaction mixture can be cooled and, if desired, filtered, and the solvent and potentially present excess alkyl halide can be removed by way of distillation. The product can be isolated by way of ball tube distillation, for example, and purified by way of column chromatography. The compound of general formula (II) thus obtained is preferably mixed with a sulfating agent, and in particular chlorosulfonic acid, in a suitable solvent, such as diethyl ether, in molar ratios up to 1:1, and in particular of 1:1.1 to 1:2, and is stirred until the reaction has been completed, in general at room temperature. Thereafter, the reaction mixture can be neutralized using aqueous MOH solution, wherein M has the meaning indicated above, and the solvent can preferably be removed by way of distillation to such an extent that the product begins to precipitate. Extraction preferably takes place by way of a suitable solvent, such as methyl-tert-butyl ether, the organic phase is separated and, if necessary, washed with aqueous saline solution, the solvent is removed by way of distillation, and the resulting residue, if desired, is dissolved in a suitable solvent, such as methanol, the solution is filtered, and the solvent is removed by way of distillation.

The surfactants according to the invention are excellently suited as ingredients in washing and cleaning agents, cosmetics such as shampoos, toothpastes, and for the remaining fields of application in which previously anionic surfactants have customarily been used, such as in the food industry, geoscience, tertiary crude oil recovery, polymer technology, metal working, photography, paper recycling, tool cleaning and firefighting.

Particularly good results are achieved when these are used in washing and cleaning agents, so that the present invention furthermore relates to the use of anionic surfactant of general formula (I) for producing washing or cleaning agents, to the use of an anionic surfactant of general formula (I) for increasing the performance of washing or cleaning agents when washing laundry or cleaning hard surfaces, and to washing or cleaning agents that comprise a surfactant of general formula (I).

DETAILED DESCRIPTION OF THE INVENTION

An agent according to the invention preferably comprises 1 wt. % to 99 wt. %, in particular 3 wt. % to 85 wt. %, and particularly preferably 5 wt. % to 65 wt. % of the surfactant of general formula (I).

In addition to the anionic surfactant of general formula (I), the washing or cleaning agent can comprise further ingredients that further improve the application-related and/or aesthetic properties of the agent. Within the scope of the present invention, the agent preferably additionally comprises one or more substances from the group consisting of non-ionic surfactants, anionic surfactants, builders, bleaching agents, bleach activators, enzymes, electrolytes, pH-setting agents, perfumes, perfume carriers, fluorescing agents, dyes, hydrotropic substances, suds suppressors, anti-redeposition agents, graying inhibitors, shrinkage preventers, anti-wrinkle agents, dye transfer inhibitors, antimicrobial active ingredients, non-aqueous solvents, germicides, fungicides, antioxidants, preservatives, corrosion inhibitors, antistatic agents, bittering agents, ironing aids, repellents and impregnating agents, active skin care ingredients, swelling and anti-slip agents, softening components and UV absorbers.

In addition to the anionic surfactant of general formula (I), the agent according to the invention preferably comprises up to 99 wt. %, in particular 2 wt. % to 85 wt. %, and particularly preferably 5 wt. % to 65 wt. % further surfactants, wherein the additionally present surfactants preferably can likewise be obtained from renewable resources.

The agent according to the invention can comprise non-ionic surfactants. Suitable non-ionic surfactants include alkoxylated fatty alcohols, alkoxylated fatty acid alkyl esters, fatty acid amides, alkoxylated fatty acid amides, polyhydroxy fatty acid amides, alkylphenol polyglycol ethers, amine oxides, alkylpolyglucosides and mixtures thereof.

Preferred alkoxylated fatty alcohols are ethoxylated, in particular primary alcohols preferably having 8 to 18 carbon atoms, and on average 4 to 12 moles ethylene oxide (EO) per mole of alcohol, in which the alcohol residue is linear. In particular, alcohol ethoxylates having 12 to 18 carbon atoms, for example from coconut, palm, tallow fatty or oleyl alcohol, and an average of 5 to 8 EO per mole of alcohol are particularly preferred. The preferred ethoxylated alcohols include, for example, $C_{12-14}$ alcohols having 4 EO or 7 EO, $C_{9-11}$ alcohols having 7 EO, $C_{12-18}$ alcohols having 5 EO or 7 EO, and mixtures thereof. The indicated degrees of ethoxylation represent statistical averages that can correspond to an integer or a fractional number for a specific product. Preferred alcohol ethoxylates exhibit a restricted distribution of homologs (narrow range ethoxylates, NRE). In addition to these non-ionic surfactants, fatty alcohols having more than 12 EO can also be used. Examples of these are tallow fatty alcohol having 14 EO, 25 EO, 30 EO, or 40 EO. According to the invention, it is also possible to use non-ionic surfactants that contain EO and PO groups together in the molecule. Also suitable is a mixture of a (more strongly) branched ethoxylated fatty alcohol and an unbranched ethoxylated fatty alcohol, such as a mixture of a $C_{16-18}$ fatty alcohol having 7 EO and 2-propylheptanol having 7 EO. The amount of non-ionic surfactant is preferably up to 25 wt. %, and in particular 1 wt. % to 20 wt. %, wherein the information in percent by weight, here and hereafter, is based on the total washing agent, unless indicated otherwise.

Possibly additionally present anionic surfactants comprise alkyl benzene sulfonic acid salts, olefin sulfonic acid salts, $C_{12-18}$ alkane sulfonic acid salts, salts of sulfuric acid monoesters with a fatty alcohol, a fatty acid soap, salts of sulfuric acid monoesters with an ethoxylated fatty alcohol, or a mixture of two or more of these anionic surfactants.

Surfactants of the sulfonate type that can be used are, for example, $C_{9-13}$ alkylbenzene sulfonates, olefin sulfonates, which is to say mixtures of alkene and hydroxyalkane sulfonates, and disulfonates, as they are obtained, for example, from $C_{12-18}$ having a terminal or internal double bond by way of sulfonation with gaseous sulfur trioxide and subsequent alkaline or acid hydrolysis of the sulfonation products. Also suitable are $C_{12-18}$ alkane sulfonates and the esters of α-sulfofatty acids (ester sulfonates), for example the α-sulfonated methyl esters of hydrogenated coconut, palm kernel or tallow fatty acids.

The salts of the sulfuric acid half-esters of $C_{12}$-$C_{18}$ fatty alcohols, for example from coconut fatty alcohol, tallow fatty alcohol, lauryl, myristyl, cetyl or stearyl alcohol, or of $C_{10}$-$C_{20}$ oxo alcohols and the half-esters of secondary alcohols having this chain length are preferred alk(en)yl sulfates. From a washing perspective, the $C_{12}$-$C_{16}$ alkyl sulfates, $C_{12}$-$C_{15}$ alkyl sulfates, and $C_{14}$-$C_{15}$ alkyl sulfates are preferred.

Fatty alcohol ether sulfates, such as the sulfuric acid monoesters of straight-chain or branched $C_{7-21}$ alcohols ethoxylated with 1 to 6 moles of ethylene oxide, such as 2-methyl-branched $C_{9-11}$ alcohols having, on average, 3.5 moles ethylene oxide (EO) or $C_{12-18}$ fatty alcohols having 1 to 4 EO, are also suited.

Further suitable anionic surfactants are fatty acid soaps. Saturated and unsaturated fatty acid soaps are suitable, such as the salts of lauric acid, myristic acid, palmitic acid, stearic acid, (hydrogenated) erucic acid and behenic acid, and in particular soap mixtures derived from natural fatty acids, such as coconut, palm kernel, olive oil, or tallow fatty acids.

The additional anionic surfactants, including the fatty acid soaps, may be present in the form of the sodium, potassium, magnesium or ammonium salts thereof. The anionic surfactants are preferably present in the form of the sodium salts or ammonium salts thereof. Amines that may be used for neutralization preferably include choline, triethylamine, monoethanolamine, diethanolamine, triethanolamine, methylethylamine, or a mixture thereof, wherein monoethanolamine is preferred. In a particularly preferred embodiment, the agent comprises alkyl benzene sulfonic acid neutralized with monoethanolamine, and in particular $C_{9-13}$ alkyl benzene sulfonic acid, and/or fatty acid neutralized with monoethanolamine, in particular when the agent is present in liquid form.

The content of additional anionic surfactant, if the same is present, in the agent according to the invention is preferably up to 30 wt. %, and in particular 1 wt. % to 25 wt. %.

An agent according to the invention preferably comprises at least one water-soluble and/or water-insoluble, organic and/or inorganic builder. The water-soluble organic builder substances include polycarboxylic acids, in particular citric acid and saccharic acids, monomeric and polymeric aminopolycarboxylic acids, in particular glycine diacetic acid, methylglycine diacetic acid, nitrilotriacetic acid, iminodisuccinates such as ethylenediamine-N,N'-disuccinic acid and hydroxyiminodisuccinates, ethylenediaminetetraacetic acid and polyaspartic acid, polyphosphonic acids, in particular aminotris(methylenephosphonic acid), ethylenediaminetetrakis(methylenephosphonic acid), lysine tetra(methylenephosphonic acid) and 1-hydroxyethane-1,1-diphosphonic acid, polymeric hydroxy compounds such as dextrin and polymeric (poly-)carboxylic acids, in particular polycarboxylates accessible by oxidation of polysaccharides, polymeric acrylic acids, methacrylic acids, maleic acids, and mixed polymers of the same, which may also have small fractions of polymerizable substances having no carboxylic acid functionality polymerized into the same. The relative average molar mass of the homopolymers of unsaturated carboxylic acids is generally between 5,000 g/mol and 200,000 g/mol, that of the copolymers is between 2,000 g/mol and 200,000 g/mol, and preferably 50,000 g/mol to 120,000 g/mol, each based on free acid. A particularly preferred acrylic acid/maleic acid copolymer has a relative average molar mass of 50,000 to 100,000. Suitable, albeit less preferred compounds of this class are copolymers of acrylic acid or methacrylic acid with vinyl ethers, such as vinyl methyl ethers, vinyl esters, ethylene, propylene and styrene, in which the proportion of the acid is at least 50 wt. %. It is also possible to use terpolymers comprising two unsaturated acids and/or the salts thereof as the monomers, and vinyl alcohol and/or a vinyl alcohol derivative or a carbohydrate as the third monomer, as water-soluble organic builder substances. The first acidic monomer or the salt thereof is derived from a monoethylenically unsaturated $C_3$-$C_8$ carboxylic acid and preferably from a $C_3$-$C_4$ monocarboxylic acid, in particular from (meth)acrylic acid. The second acidic monomer or the salt thereof can be a derivative of a $C_4$-$C_8$ dicarboxylic acid, wherein maleic acid is particularly preferred. The third monomeric unit is formed in this case by vinyl alcohol and/or preferably an esterified vinyl alcohol. In particular, vinyl alcohol derivatives which represent an ester of short-chain carboxylic acids, for example of $C_1$-$C_4$ carboxylic acids, with vinyl alcohol are preferred. Preferred polymers comprise 60 wt. % to 95 wt. %, in particular 70 wt. % to 90 wt. %, (meth)acrylic acid or (meth)acrylate, and particularly preferably acrylic acid or acrylate, and maleic acid or maleinate, and 5 wt. % to 40 wt. %, preferably 10 wt. % to 30 wt. %, vinyl alcohol and/or vinyl acetate. Most particularly preferred are polymers in which the weight ratio of (meth)acrylic acid or (meth)acrylate to maleic acid or maleinate ranges between 1:1 and 4:1, preferably between 2:1 and 3:1, and in particular 2:1 and 2.5:1. Both the amounts and the weight ratios are based on the acids. The second acidic monomer or the salt thereof can also be a derivative of an allyl sulfonic acid, which at the 2-position is substituted with an alkyl functional group, preferably a $C_1$-$C_4$ alkyl functional group, or an aromatic functional group, which is preferably derived from benzene or benzene derivatives. Preferred terpolymers contain 40 wt. % to 60 wt. %, in particular 45 wt. % to 55 wt. %, (meth)acrylic acid or (meth)acrylate, particularly preferably acrylic acid or acrylate, 10 wt. % to 30 wt. %, preferably 15 wt. % to 25 wt. %, methallyl sulfonic acid or methallyl sulfonate, and, as the third monomer, 15 wt. % to 40 wt. %, preferably 20 wt. % to 40 wt. % of a carbohydrate. This carbohydrate can be a monosaccharide, disaccharide, oligosaccharide or polysaccharide, for example, wherein monosaccharides, disaccharides or oligosaccharides are preferred. Sucrose is particularly preferred. As a result of the use of the third monomer, predetermined breaking points are presumably introduced into the polymer, which are responsible for the good biodegradability of the polymer. These terpolymers generally have a relative average molar mass between 1,000 g/mol and 200,000 g/mol, and preferably between 200 g/mol and 50,000 g/mol. Further preferred copolymers are those that contain acrolein and acrylic acid/acrylic acid salts or vinylacetate as monomers. The organic builders can be used in the form of aqueous solutions, and preferably in the form of 30 to 50 percent by weight aqueous solutions, in particular for the production of liquid agents. All aforementioned acids are generally used in the form of the water-soluble salts thereof, and in particular of the alkali salts thereof.

Such organic builders can be present in amounts up to 40 wt. %, in particular up to 25 wt. %, and preferably from 1 wt. % to 8 wt. %, if desired. Amounts in the upper half of the aforementioned ranges are preferably used for pasty or liquid, in particular hydrous, agents.

Water-soluble inorganic builder materials that can be used are in particular polyphosphates, and preferably sodium triphosphate. Water-insoluble inorganic builder materials that are used are in particular crystalline or amorphous, water-dispersible alkali aluminosilicates, in amounts not above 25 wt. %, preferably from 3 wt. % to 20 wt. %, and in particular in amounts from 5 wt. % to 15 wt. %. Among these, the crystalline sodium aluminosilicates in washing agent quality, in particular zeolite A, zeolite P and zeolite MAP, and optionally zeolite X, are preferred. Amounts close to the aforementioned upper limit are preferably used in solid, particulate agents. Suitable aluminosilicates in particular do not comprise any particles having a particle size above 30 µm, and preferably have a content of at least 80 wt. % of particles having a size of less than 10 µm. The calcium-binding capacity is generally in the range of 100 to 200 mg CaO per gram.

In addition or as an alternative to the described water-insoluble aluminosilicate and alkali carbonate, further water-soluble inorganic builder materials may be present. In addition to the polyphosphates such as sodium triphosphate, these include in particular the water-soluble crystalline and/or amorphous alkali silicate builders. The agents preferably comprise such water-soluble inorganic builder materials in amounts of 1 wt. % to 20 wt. %, and in particular 5 wt. % to 15 wt. %. The alkali silicates that can be used as builder materials preferably have a molar ratio of alkali oxide to $SiO_2$ of less than 0.95, in particular of 1:1.1 to 1:12 and can be present in amorphous or crystalline form. Preferred alkali silicates are sodium silicates, and in particular the amorphous sodium silicates, having a molar ratio of $Na_2O:SiO_2$ of 1:2 to 1:2.8. Crystalline silicates, which may be present either alone or in a mixture with amorphous silicates, that are used are preferably crystalline phyllosilicates of general formula $Na_2Si_xO_{2x+1}\cdot yH_2O$, where x, the so-called module, is a number from 1.9 to 4, and y is a number from 0 to 20, and preferred values for x are 2, 3 or 4. Preferred crystalline phyllosilicates are those in which x in the above-mentioned general formula takes on the value 2 or 3. In particular, both β- and δ-sodium disilicates $(Na_2Si_2O_5\cdot yH_2O)$ are preferred. Practically anhydrous crystalline alkali silicates, produced from amorphous alkali silicates, of the above general formula, in which x denotes a number from 1.9 to 2.1, can also be used in the detergents. In a further preferred embodiment, a crystalline sodium phyllosilicate having a module of 2 to 3 is used, as it can be produced from sand and soda. Sodium silicates having a module in the range from 1.9 to 3.5 are used in a further embodiment. In a preferred embodiment of such agents, a granular compound composed of alkali silicate and alkali carbonate is used, as is commercially available under the name Nabion® 15, for example.

Possible suitable peroxide bleaching agents include in particular organic peroxy acids or peracid salts of organic acids, such as phthalimidopercaproic acid, perbenzoic acid, monoperoxyphthalic acid and diperdodecanoic diacid and the salts thereof, such as magnesium monoperoxyphthalate, diacyl peroxides, hydrogen peroxide and inorganic salts giving off hydrogen peroxide under the usage conditions, such as alkali perborate, alkali percarbonate and/or alkali persilicate, and hydrogen peroxide clathrates, such as $H_2O_2$ urea adducts. Hydrogen peroxide may also be created by way of an enzymatic system, which is to say an oxidase and the substrate thereof. To the extent that solid peroxygen compounds are to be used, these may be used in the form of powders or granules, which may also be coated in the manner known per se. The use of alkali percarbonate, alkali perborate monohydrate or hydrogen peroxide is particularly preferred. A washing agent that can be used within the scope of the invention comprises a peroxide bleaching agent in amounts of preferably up to 60 wt. %, in particular of 5 wt. % to 50 wt. %, and particularly preferably of 15 wt. % to 30 wt. %, or alternatively of 2.5 wt. % to 20 wt. %, wherein the particularly preferred peroxide bleaching agent in liquid agents is hydrogen peroxide, and in solid agents it is sodium percarbonate. Peroxide bleaching agent particles preferably have a particle size in the range of 10 μm to 5000 μm, and in particular of 50 μm to 1000 μm, and/or a density of 0.85 g/cm$^3$ to 4.9 g/cm$^3$, and in particular of 0.91 g/cm$^3$ to 2.7 g/cm$^3$.

In particular, compounds that, under perhydrolysis conditions, yield optionally substituted perbenzoic acid and/or aliphatic peroxocarboxylic acids having 1 to 12 carbon atoms, and in particular 2 to 4 carbon atoms, either alone or in mixtures, can be used as the bleach-activating compound yielding peroxocarboxylic acid under perhydrolysis conditions. Suitable bleach activators are those that carry O- and/or N-acyl groups, in particular having the described carbon atomic number and/or optionally substituted benzoyl groups. Polyacylated alkylenediamines, in particular tetraacetyl ethylene diamine (TAED), acylated glycolurils, in particular tetraacetyl glycoluril (TAGU), acylated triazine derivatives, in particular 1,5-diacetyl-2,4-dioxohexahydro-1,3,5-triazine (DADHT), N-acylimides, in particular N-nonanoyl succinimide (NOSI), acylated phenolsulfonates or phenolcarboxylates or the sulfonic or carboxylic acids of these, in particular nonanoyl or iso-nonanoyl or lauroyl oxybenzene sulfonate (NOBS or iso-NOBS or LOBS), or decanoyloxybenzoate (DOBA), the formal carboxylic acid ester derivatives thereof, such as 4-(2-decanoyloxyethoxy-carbonyloxy)benzene sulfonate (DECOBS), acylated polyhydric alcohols, in particular triacetin, ethylene glycol diacetate and 2,5-diacetoxy-2,5-dihydrofuran, and acetylated sorbitol and mannitol and the mixtures thereof (SORMAN), acylated sugar derivatives, in particular penta-acetyl glucose (PAG), penta-acetyl fructose, tetra-acetyl xylose and octa-acetyl lactose, acetylated, optionally N-alkylated glucamine and gluconolactone, and/or N-acylated lactams, for example N-benzoyl caprolactam, are preferred.

In addition to or instead of the compounds that, under perhydrolysis conditions, form peroxocarboxylic acids, further bleach-activating compounds, such as nitriles, which yield perimidic acids under perhydrolysis conditions, may be present. These include in particular aminoacetonitrile derivatives comprising a quaternized nitrogen atom according to formula

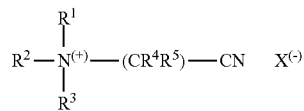

in which $R^1$ denotes —H, —CH$_3$, a C$_{2-24}$ alkyl or alkenyl functional group, a substituted C$_{1-24}$ alkyl functional group or C$_{2-24}$ alkenyl functional group comprising at least one substituent from the group —Cl, —Br, —OH, —NH$_2$, CN and —N$^{(+)}$—CH$_2$—CN, an alkyl or alkenyl aryl functional group having a C$_{1-24}$ alkyl group, or a substituted alkyl or alkenyl aryl functional group having at least one, preferably two, optionally substituted C$_{1-24}$ alkyl groups and optionally further substituents on the aromatic ring, $R^2$ and $R^3$, independently of one another, are selected from —CH$_2$—CN, —CH$_3$, —CH$_2$—CH$_3$, —CH$_2$—CH$_2$—CH$_3$, —CH(CH$_3$)—CH$_3$, —CH$_2$—OH, —CH$_2$—CH$_2$—OH, —CH(OH)—CH$_3$, —CH$_2$—CH$_2$—CH$_2$—OH, —CH$_2$—CH(OH)—CH$_3$, —CH(OH)—CH$_2$—CH$_3$, —(CH$_2$CH$_2$—O)$_n$H, where n=1, 2, 3, 4, 5 or 6, $R^4$ and $R^5$, independently of one another, have a meaning stated above for R$_1$, $R^2$ or $R^3$, wherein at least two of the aforementioned functional groups, in particular $R^2$ and $R^3$, may be linked to one another so as to close the ring, including the nitrogen atom and optionally further heteroatoms, and then preferably form a morpholino ring, and X is a charge-equalizing anion, preferably selected from benzene sulfonate, toluene sulfonate, cumol sulfonate, the C$_{9-15}$ alkylbenzene sulfonates, the C$_{1-20}$ alkyl sulfates, the C$_{8-22}$ carboxylic acid methyl ester sulfonates, sulfate, hydrogen sulfate, and the mixture thereof, can be used. Bleach activators forming peroxocarboxylic acids or perimidic acids under perhydrolysis conditions are preferably present in amounts up to 25 wt. %, and in particular 0.1 wt. % to 10 wt. % in the agents according to the invention. Bleach activator particles preferably have a particle size in the range of 10 μm to 5000 μm, and in particular of 50 μm to 1000 μm, and/or a density of 0.85 g/cm$^3$ to 4.9 g/cm$^3$, and in particular of 0.91 g/cm$^3$ to 2.7 g/cm$^3$.

It is possible for bleach-catalyzing transition metal complexes to be present, either in addition to or instead of the aforementioned bleach activators. These are preferably selected among the cobalt, iron, copper, titanium, vanadium, manganese and ruthenium complexes. Possible ligands in such transition metal complexes are either inorganic or organic compounds, which in addition to carboxylates, include in particular compounds having primary, secondary and/or tertiary amine and/or alcohol functions, such as pyridine, pyridazine, pyrimidine, pyrazine, imidazole, pyrazole, triazole, 2,2'-bispyridyl amine, tris-(2-pyridylmethyl) amine, 1,4,7-triazacyclononane, 1,4,7-trimethyl-1,4,7-triazacyclononane, 1,5,9-trimethyl-1,5,9-triazacyclododecane, (bis-((1-methylimidazol-2-yl)-methyl))-(2-pyridylmethypamine, N,N'-(bis-(1-methylimidazol-2-yl)-methyl)ethylenediamine, N-bis-(2-benzimidazolylmethyl)aminoethanol, 2,6-bis-(bis-(2-benzimidazolylmethyl)aminomethyl)-4-methylphenol, N,N,N',N'-tetrakis-(2-benzimidazolylmethyl)-2-hydroxy-1,3-diaminopropane, 2,6-bis-(bis-(2-pyridyl-methyl)aminomethyl)-4-methylphenol, 1,3-bis-(bis-(2-benzimidazolylmethyl)aminomethyl)benzene, sorbitol, mannitol, erythritol, adonitol, inositol, lactose, and optionally substituted salenes, porphins and porphyrins. The inorganic neutral ligands include in particular ammonia and water. If not all coordination sites of the central transition metal atom are occupied by neutral ligands, the complex comprises further, preferably anionic and, among these, in particular monodentate or bidentate, ligands. These include in particular the halides, such as fluoride, chloride, bromide and iodide, and the $(NO_2)^-$ group, which is to say a nitro ligand or a nitrito ligand. The $(NO_2)^-$ group can also be bound to a transition metal in a chelating manner, or it may asymmetrically or $\mu^1$-O bridge two transition metal atoms. In addition to the above-mentioned ligands, the transition metal complexes can carry further ligands, which generally have simpler structures, and in particular monovalent or polyvalent anionic ligands. For example, nitrate, acetate, trifluoroacetate, formate, carbonate, citrate, oxalate, perchlorate and complex anions such as hexafluorophosphate may be used. The anionic ligands are to ensure the charge equalization between the central transition metal atom and the ligand system. The presence of oxo ligands, peroxo ligands and imino ligands is also possible. In particular, these ligands may also have a bridging effect, whereby multinuclear complexes are created. In the case of bridged, binuclear complexes, the two metal atoms in the complex do not have to be identical. It is also possible to use binuclear complexes in which the two central transition metal atoms have differing oxidation numbers. If anionic ligands are absent or the presence of anionic ligands does not result in charge equalization in the complex, anionic counterions are present in the transition metal complex compounds to be used according to the invention, which neutralize the cationic transition metal complex. These anionic counterions include in particular nitrate, hydroxide, hexafluorophosphate, sulfate, chlorate, perchlorate, the halides such as chloride, or the anions of carboxylic acids such as formate, acetate, oxalate, benzoate or citrate. Examples of transition metal complex compounds that may be used include [N,N'-bis[(2-hydroxy-5-vinylphenyl)-methylene]-1,2-diamino-cyclohexane]-manganese-(III)-chloride, [N,N'-bis[(2-hydroxy-5-nitrophenyl)-methylene]-1,2-diamino-cyclohexane]-manganese-(lll)-acetate, [N,N'-bis[(2-hydroxyphenyl)-methylene]-1,2-phenylendiamine]-manganese-(lll)-acetate, [N,N'-bis[(2-hydroxyphenyl)-methylene]-1,2-diaminocyclohexane]-manganese-(lll)-chloride, [N,N'-bis[(2-hydroxyphenyl)-methylene]-1,2-diaminoethane]-manganese-(lll)-chloride, [N,N'-bis[(2-hydroxy-5-sulfonatophenyl)-methylene]-1,2-diaminoethane]-manganese-(lll)-chloride, manganese-oxalato complexes, nitropentamminecobalt(lll) chloride, nitritopentamminecobalt(lll) chloride, hexamminecobalt(lll) chloride, chloropentamminecobalt(lll) chloride, and the peroxo complex $[(NH_3)_5Co-O-O-Co(NH_3)_5]Cl_4$.

Enzymes that can be used in the agents include those of the class of proteases, amylases, lipases, cutinases, pullulanases, hemicellulases, cellulases, oxidases, laccases and peroxidases, and the mixtures thereof. Particularly suited are enzymatic active ingredients obtained from fungi or bacteria, such as *Bacillus subtilis, Bacillus licheniformis, Bacillus lentus, Streptomyces griseus, Humicola lanuginosa, Humicola insolens, Pseudomonas pseudoalcaligenes, Pseudomonas cepacia* or *Coprinus cinereus*. The enzymes can be adsorbed on carrier substances and/or be embedded in coating substances to protect them against premature inactivation. These are preferably present in the washing or cleaning agents according to the invention in amounts up to 5 wt. %, and in particular of 0.002 wt. % to 4 wt. %. If the agent according to the invention comprises protease, this preferably has a proteolytic activity in the range of approximately 100 PE/g to approximately 10,000 PE/g, and in particular 300 PE/g to 8000 PE/g. If several enzymes are to be used in the agent according to the invention, this may be carried out by incorporating two or more enzymes that are separate or separately formulated in the known manner, or by two or more enzymes that are formulated together in granules.

To set a desired pH value that does not result on its own by virtue of mixing the remaining components, the agents according to the invention can comprise system-compatible and environmentally friendly acids, in particular citric acid, acetic acid, tartaric acid, malic acid, lactic acid, glycolic acid, succinic acid, glutaric acid and/or adipic acid, but also mineral acids, in particular sulfuric acid, or bases, in particular ammonium hydroxides or alkali hydroxides. Such pH regulators are preferably present in the agents according to the invention in amounts not above 20 wt. %, and in particular of 1.2 wt. % to 17 wt. %.

The task of graying inhibitors is to maintain the dirt dissolved from the textile fibers suspended in the liquor. Water-soluble colloids, usually of an organic nature, are suitable for this purpose, such as starch, sizing material, gelatin, salts of ether carboxylic acids or ether sulfonic acids of starch or cellulose, or salts of acidic sulfuric acid esters of cellulose or starch. Water-soluble, acid group-containing polyamides are also suitable for this purpose. Furthermore, starch derivatives other than those mentioned above may be used, for example aldehyde starches. The use of cellulose ethers, such as carboxymethyl cellulose (Na salt), methyl cellulose, hydroxyalkyl cellulose and mixed ethers, such as methyl hydroxyethyl cellulose, methyl hydroxypropyl cellulose, methyl carboxymethyl cellulose and the mixtures thereof, for example in amounts of 0.1 to 5 wt. %, based on the agents, is preferred.

If desired, the agents can comprise a customary dye transfer inhibitor, preferably in amounts up to 2 wt. %, and in particular of 0.1 wt. % to 1 wt. %, which in a preferred embodiment is selected from the polymers of vinylpyrrolidone, vinylimidazole, vinylpyridine-N-oxide, or the copolymers of these. It is possible to use both polyvinylpyrrolidones having molecular weights of 15,000 g/mol to 50,000 g/mol and polyvinylpyrrolidones having higher molecular weights of more than 1,000,000 g/mol, and in particular of 1,500,000 g/mol to 4,000,000 g/mol, for example, N-vinylimidazole/N-vinylpyrrolidone copolymers, polyvinyloxazolidones, copolymers based on vinyl monomers and carboxylic acid amides, pyrrolidone group-comprising polyesters and polyamides, grafted polyamidoamines and polyethylene imines, polyamine-N-oxide polymers and polyvinyl alcohols. However, it is also possible to use enzymatic systems, comprising a peroxidase and hydrogen peroxide or a substance yielding hydrogen peroxide in water. The addition of a mediator compound for the peroxidase, for example of an acetosyringone, a phenol derivative or a phenothiazine or phenoxazine, is preferred in this case, wherein in addition the above-mentioned polymeric dye transfer inhibitor active ingredients can also be used. Polyvinylpyrrolidone preferably has an average molar mass in the range of 10,000 g/mol to 60,000 g/mol, and in particular in the range of 25,000 g/mol to 50,000 g/mol. Among the copolymers, those composed of vinylpyrrolidone and vinylimidazole in a molar ratio of 5:1 to 1:1, having an average molar mass in the range of 5,000 g/mol to 50,000 g/mol, and in particular of 10,000 g/mol to 20,000 g/mol, are preferred. In preferred embodiments of the invention, however, the washing agents are free from such added dye transfer inhibitors.

Washing agents can comprise derivatives of diaminostilbene disulfonic acid or the alkali metal salts thereof, for example, as optical brighteners, although they are preferably free from optical brighteners when used as washing agents for colored textiles. For example, salts of 4,4'-bis(2-anilino-4-morpholino-1,3,5-triazinyl-6-amino)stilbene-2,2'-disulfonic acid or similarly structured compositions are suitable, which carry a diethanolamino group, a methylamino group, an anilino group or a 2-methoxyethylamino group instead of the morpholino group. Moreover, brighteners of the type of substituted diphenylstyryls can be present, for example the alkali salts of 4,4'-bis(2-sulfostyryl)biphenyl, 4,4'-bis(4-chloro-3-sulfostyryl)biphenyl, or 4-(4-chlorostyryl)-4'-(2-sulfostyryl)biphenyls. It is also possible to use mixtures of the aforementioned optical brighteners.

In particular when used with mechanical processes, it may be advantageous to add customary suds suppressors to the agents. For example, soaps of natural or synthetic origin having a high content of $C_{18}$-$C_{24}$ fatty acids are suitable suds suppressors. Suitable non-surfactant-type suds suppressors are, for example, organopolysiloxanes and the mixtures thereof with micro-fine, optionally silanized silicic acid and paraffins, waxes, microcrystalline waxes and the mixtures thereof with silanized silicic acid or bis-fatty acid alkylene diamides. Advantageously, mixtures of different suds suppressors are also used, for example those composed of silicones, paraffins or waxes. The suds suppressors, and in particular silicone-comprising and/or paraffin-comprising suds suppressors, are preferably bound to a granular carrier substance that is soluble or dispersible in water. In particular, mixtures of paraffins and ethylene distearylamide are preferred.

In a preferred embodiment, the agent according to the invention is particulate and, in addition to the surfactant of general formula (I), comprises builders, in particular in an amount in the range of 1 wt. % to 60 wt. %.

In a further preferred embodiment, an agent according to the invention is liquid and comprises 1 wt. % to 90 wt. %, in particular 10 wt. % to 85 wt. %, preferably 25 wt. % to 75 wt. %, and particularly preferably 35 wt. % to 65 wt. % water, water-miscible solvent or a mixture of water and water-miscible solvent. Water-miscible solvents include, for example, monohydric alcohols comprising 1 to 4 carbon atoms, in particular methanol, ethanol, isopropanol and tert-butanol, diols and triols comprising 2 to 4 carbon atoms, in particular ethylene glycol, propylene glycol and glycerol, and the mixtures thereof and ethers thereof derivable from the aforementioned compound classes. Such water-miscible solvents are preferably present in the agents according to the invention in amounts not above 30 wt. %, and in particular of 2 wt. % to 20 wt. %.

In a further preferred embodiment, the agent according to the invention is present portioned and ready-for-use in individual doses in a chamber formed of water-soluble material. A portion represents an independent dosing unit with at least one chamber, in which product to be dosed is present. A chamber is a space that is delimited by walls (by a film, for example) and can also exist without the product to be dosed (if necessary, in a changed shaped). A surface coating or a layer of a surface coating thus does not constitute a wall according to the present invention.

The walls of the chamber are made of a water-soluble material. The water solubility of the material can be determined by way of a square film of said material (film: 22×22 mm having a thickness of 76 μm) fixed with the aid of a square frame (edge length on the inside: 20 mm), according to the following measuring protocol. Said framed film is immersed in 800 ml distilled water controlled to 20° C. in a 1-liter beaker glass having a circular base area (Schott, Mainz, beaker glass 1000 mL, low shape), so that the surface area of the tensioned film is arranged at a right angle with respect to the base area of the beaker glass, the upper edge of the frame is located 1 cm beneath the water surface, and the lower edge of the frame is oriented parallel to the base area of the beaker glass in such a way that the lower edge of the frame extends along the radius of the base area of the beaker glass, and the center of the lower edge of the frame is arranged above the center of the radius of the beaker glass bottom. The material dissolves, when stirred (stirring speed of magnetic stirrer 300 rpm, stirring rod: 5 cm long), within 600 seconds in such a way that individual solid particles can no longer be detected with the naked eye.

The walls of the chambers, and thus the water-soluble wrappings of the washing agents according to the invention are preferably formed by a water-soluble film material. Such water-soluble packagings can be produced using either vertical form fill sealing methods or using thermoforming methods.

The thermoforming method generally includes forming a first layer from a water-soluble film material so as to create bulges for receiving a composition therein, filling the composition into the bulges, covering the bulges that are filled with the composition with a second layer made of a water-soluble film material, and sealing the first and second layers together, at least around the bulges.

The water-soluble film material is preferably selected from polymers or polymer mixtures. The wrapping can be formed of one layer, or of two or more layers of the water-soluble film material. The water-soluble film materials of the first layer and of the further layers, if such are present, can be the same or different.

It is preferable for the water-soluble wrapping to comprise polyvinyl alcohol or a polyvinyl alcohol copolymer, and particularly preferably it consists of polyvinyl alcohol or a polyvinyl alcohol copolymer.

Water-soluble films for producing the water-soluble wrapping are preferably based on a polyvinyl alcohol, or a polyvinyl alcohol copolymer, having a molecular weight in the range of 10,000 to 1,000,000 gmol$^{-1}$, preferably of 20,000 to 500,000 gmol$^{-1}$, particularly preferably of 30,000 to 100,000 gmol$^{-1}$ and in particular of 40,000 to 80,000 gmol$^{-1}$.

The polyvinyl alcohol is typically produced by the hydrolysis of polyvinyl acetate since the direct synthesis pathway is not possible. The same applies to polyvinyl alcohol copolymers produced accordingly from polyvinyl acetate copolymers. It is preferred if at least one layer of the water-soluble wrapping comprises a polyvinyl alcohol having a degree of hydrolysis of 70 to 100 mol %, preferably 80 to 90 mol %, particularly preferably 81 to 89 mol %, and in particular 82 to 88 mol %.

Additionally, polymers selected from the group consisting of acrylic acid-containing polymers, polyacrylamides, oxazoline polymers, polystyrene sulfonates, polyurethanes, polyesters, polyethers, polylactic acid and/or mixtures of the above polymers can be added to a film material that is suitable for producing the water-soluble wrapping. The co-polymerization of monomers underlying such polymers, either individually or in mixtures of two or more, with vinyl acetate is also possible.

Preferred polyvinyl alcohol copolymers include an ethylenically unsaturated carboxylic acid, the salt thereof, or the ester thereof, in addition to vinyl alcohol. In addition to vinyl alcohol, such polyvinyl alcohol copolymers particularly preferably comprise acrylic acid, methacrylic acid, acrylic acid esters, methacrylic acid esters or mixtures thereof; among the esters, $C_{1-4}$ alkyl esters or hydroxyalkyl esters are preferred. In addition to vinyl alcohol, likewise preferred polyvinyl alcohol copolymers comprise ethylenically unsaturated dicarboxylic acids as further monomers. Suitable dicarboxylic acids are, for example, itaconic acid, maleic acid, fumaric acid and mixtures thereof, itaconic acid being particularly preferred.

Suitable water-soluble films for use in the wrappings of the water-soluble packagings according to the invention are films sold by MonoSol LLC, for example, by the designation M8630, C8400 or M8900. Other suitable films include films by the designation Solublon® PT, Solublon® GA, Solublon® KC or Solublon® KL from Aicello Chemical Europe GmbH, or the VF-HP films from Kuraray.

The washing or cleaning agent portion, comprising the washing or cleaning agent and the water-soluble wrapping, can comprise one or more chambers. The water-soluble wrappings comprising one chamber can have a substantially dimensionally stable spherical, spheroid-shaped, cubic, cuboid or pillow-shaped design having a circular, elliptic, square or rectangular basic shape. The agent can be present in one or more chambers, if present, of the water-soluble wrapping.

In a preferred embodiment, the water-soluble wrapping comprises two chambers. In this embodiment, the two chambers can each contain a solid partial composition, or can each contain a liquid partial composition, or the first chamber contains a liquid partial composition and the second chamber contains a solid partial composition.

The proportions of the agents contained in the different chambers of a water-soluble wrapping comprising two or more chambers can have the same composition. Preferably, however, the agents in a water-soluble wrapping comprising at least two chambers have partial compositions that differ in at least one ingredient and/or in the content of at least one ingredient. A partial composition of such agents according to the invention preferably comprises an enzyme and/or bleach activator, and a further partial composition present separately therefrom comprises a peroxide bleaching agent, wherein the first partial composition, in particular, does not comprise a peroxide bleaching agent, and the second partial composition, in particular, does not comprise an enzyme and does not comprise a bleach activator.

The portioned packaging in a water-soluble wrapping enables the user to place one or, if desired, multiple, preferably one, of the portions into the washing machine or dishwasher for use, and in particular in the detergent dispenser of a washing machine, or in a receptacle for carrying out a manual washing or cleaning process. Such portioned packagings meet the consumer's desire for simplified dosing. After water is added, the wrapping material dissolves, whereby the ingredients are released and able to develop the action thereof in the liquor. A water-soluble wrapped portion preferably weighs 10 g to 35 g, in particular 12 g to 28 g, and particularly preferably 12 g to 15 g, wherein the proportion of the water-soluble wrapping accounts for 0.3 g to 2.5 g, and in particular 0.7 g to 1.2 g, in the weight information.

The production of solid agents according to the invention does not pose any difficulties and be carried out in the known manner, for example by way of spray drying or granulation, wherein enzymes and potential further thermally sensitive ingredients, such as bleaching agents, are optionally added separately later. To produce agents having increased bulk density, in particular in the range from 650 g/L to 950 g/L, a method comprising an extrusion step is preferred.

Liquid or pasty agents according to the invention in the form of solutions comprising water customary solvents are generally produced by simple mixing of the ingredients, which can be placed into an automatic mixer in substance or as a solution.

EXAMPLES

Example 1: Production of 4-(3-hydroxypropyl)-guaiacol from Wood

As described in Angew. Chem. Int. Ed. 2014, 53, 8634 to 8639, spruce wood pellets and Raney nickel were suspended in a 2-propanol/water mixture and heated in the autoclave for 3 hours to 180° C. The resultant organic oil was separated from the remaining solids, and from this 4-(3-hydroxypropyl)-guaiacol was quantitatively isolated by way of ball tube distillation.

Example 2: Production of Surfactants According to the Invention 5 mmol 4-(3-hydroxypropyl)-guaiacol and 10 mmol 1-n-dodecyl bromide in 125 ml dry acetone were heated under reflux until boiling in the presence of 15 mmol potassium carbonate for 19 hours under an Ar atmosphere. Thereafter, the reaction mixture was cooled, filtered over Celite, the organic solvent was removed by way of distillation at normal pressure, and the excess alkyl bromide was removed by way of distillation at reduced pressure. The product was isolated by way of ball tube distillation and purified by way of column chromatography. This resulted in a yield of 91 percent of 3-(4-(dodecyloxy-3-methoxyphenyl)propan-1-ol.

1 mmol of the 3-(4-(dodecyloxy-3-methoxyphenyl)propan-1-ol thus obtained was reacted with 1 mmol chlorosulfonic acid in 40 ml dry diethyl ether for 2 hours at room temperature. Thereafter, the reaction mixture was neutralized with 2 M aqueous NaOH, and the solvent was removed by way of distillation to such an extent that the product started to crystallize out. Thereafter, the mixture was extracted with methyl-tert-butyl ether, and the organic phase was separated and washed with aqueous saline solution. The solvent was removed, and the resulting solid was dissolved in methanol. The solution was filtered over Celite and concentrated to dryness. This resulted in a yield of 91% of surfactant T1 of general formula (I), where $R^1$=n-dodecyl, $R^2$=OCH$_3$, $R^3$=H, and M=Na.

By using 2-methoxy-4-(3-hydroxypropyl)-guaiacol and corresponding alkyl bromides, analogously the surfactants according to general formula (I), where $R^1$=n-decyl, $R^2$=OCH$_3$, and $R^3$=H (T2), $R^1$=n-tetradecyl, $R^2$=OCH$_3$, and $R^3$=H (T3), were obtained.

Example 3: Measurement of the Critical Micelle Concentration (CMC)

The CMC of the surfactants produced in Example 2 was determined by measuring the surface tension of an aqueous solution of the substances as a function of the concentration at 25° C. and a pH of 8.5. For comparison, the CMC of petrochemically produced Na dodecyl benzene sulfonate (V1) was determined under identical conditions.

TABLE 1

| CMC values | |
| --- | --- |
| Substance | CMC (g/l) |
| V1 | 0.11 |
| T1 | 0.01 |
| T2 | 0.04 |
| T3 | 0.01 |

It is apparent that the surfactants according to the invention have a considerably lower CMC than the petrochemically based surfactant.

Example 4: Measurement of the Interfacial Tension

The interfacial tension of a respective aqueous solution of the substances described in Example 3 (concentration 1 g/l in each case) over triolein at pH 8.5 and 25° C. was measured by way of the spinning drop method. After 20 minutes, the values listed in Table 2 were obtained.

TABLE 2

| Interfacial tension values | |
| --- | --- |
| Substance | γ (mN/ml) |
| V1 | 0.5 |
| T1 | 0.8 |
| T2 | 0.6 |
| T3 | 0.7 |

It is apparent that interfacial tensions of the surfactants according to the invention did not deviate significantly from those of the frequently used, petrochemically based surfactant.

What is claimed is:

1. An anionic surfactant of general formula (I),

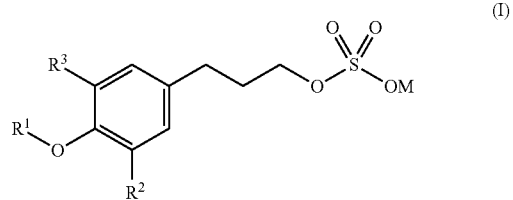

in which R' denotes a linear or branched alkyl functional group having 6 to 20 carbon atoms, $R^2$ and $R^3$, independently of one another, denote H or H$_3$CO, and M denotes hydrogen, an alkali metal or an N$^+$R$^4$R$^5$R$^6$ grouping, in which $R^4$, $R^5$ and $R^6$, independently of one another, denote hydrogen, an alkyl group having 1 to 6 carbon atoms or a hydroxyalkyl group having 2 to 6 carbon atoms.

2. A method for producing an anionic surfactant of general formula (I),

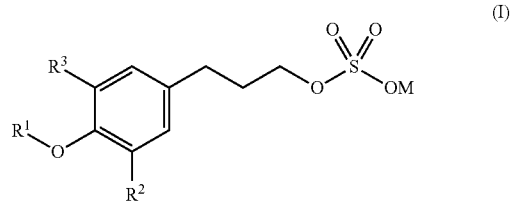

in which $R^1$ denotes a linear or branched alkyl functional group having 6 to 20 carbon atoms, $R^2$ and $R^3$, independently of one another, denote H or H$_3$CO, and M denotes hydrogen, an alkali metal or an N$^+$R$^4$R$^5$R$^6$ grouping, in which $R^4$, $R^5$ and $R^6$, independently of one another, denote hydrogen, an alkyl group having 1 to 6 carbon atoms or a hydroxyalkyl group having 2 to 6 carbon atoms, comprising the step of sulfonating a compound of general formula (II),

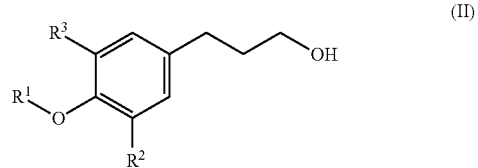

in which $R^1$ denotes a linear or branched alkyl functional group having 6 to 20 carbon atoms, $R^2$ and $R^3$, independently of one another, denote H or H$_3$CO, with a sulfating agent, and neutralization by way of subsequent reaction with MOH, wherein M denotes an alkali metal or an N$^+$R$^4$R$^5$R$^6$ grouping, in which $R^4$, $R^5$ and $R^6$, independently of one another, denote hydrogen, an alkyl group having 1 to 6 carbon atoms or a hydroxyalkyl group having 2 to 6 carbon atoms.

3. A method for producing a compound of general formula (II),

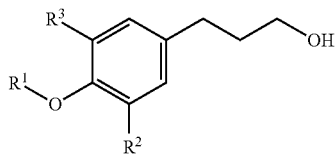

in which $R^1$ denotes a linear or branched alkyl functional group having 6 to 20 carbon atoms, le and $R^3$, independently of one another, denote H or $H_3CO$,
comprising the step of reacting a compound of general formula (III),

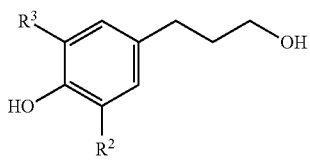

in which $R^2$ and $R^3$, independently of one another, are H or $H_3CO$,
with a compound $R^1$-Hal, in which $R^1$ denotes a linear or branched alkyl functional group having 6 to 20 carbon atoms, and Hal denotes chlorine, bromine, iodine or mixtures thereof, under alkaline conditions.

4. A washing or cleaning agent, comprising an anionic surfactant of general formula (I),

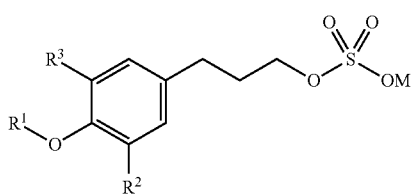

in which $R^1$ denotes a linear or branched alkyl functional group having 6 to 20 carbon atoms, $R^2$ and $R^3$, independently of one another, denote H or $H_3CO$, and M denotes hydrogen, an alkali metal or an $N^+R^4R^5R^6$ grouping, in which $R^4$, $R^5$ and $R^6$, independently of one another, denote hydrogen, an alkyl group having 1 to 6 carbon atoms or a hydroxyalkyl group having 2 to 6 carbon atoms.

5. The washing or cleaning agent according to claim 4, characterized by comprising 1 wt. % to 99 wt. % of the surfactant of general formula (I).

6. The washing or cleaning agent according to claim 4, characterized by additionally comprising up to 99 wt. %, of a further surfactant.

7. The washing or cleaning agent according to claim 4, characterized by being particulate and comprising builders.

8. The washing or cleaning agent according to claim 4, characterized by being liquid and comprising 1 wt. % to 90 wt. % water, water-miscible solvent or a mixture of water and water-miscible solvent.

9. The washing or cleaning agent according to claim 4, characterized by being present portioned and ready-for-use in individual doses in a chamber formed of water-soluble material.

10. The anionic surfactant, according to claim 1, of general formula (I),

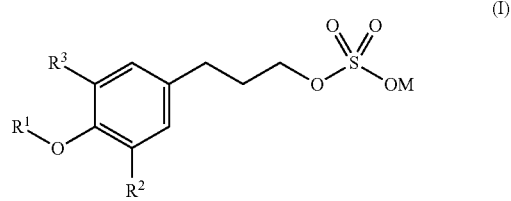

in which $R^1$ denotes a linear or branched alkyl functional group having 10 to 16 carbon atoms, $R^2$ and $R^3$, independently of one another, denote H or $H_3CO$, and M denotes hydrogen, an alkali metal or an $N^+R^4R^5R^6$ grouping, in which $R^4$, $R^5$ and $R^6$, independently of one another, denote hydrogen, an alkyl group having 1 to 6 carbon atoms or a hydroxyalkyl group having 2 to 6 carbon atoms.

11. The method according to claim 2, for producing an anionic surfactant of general formula (I),

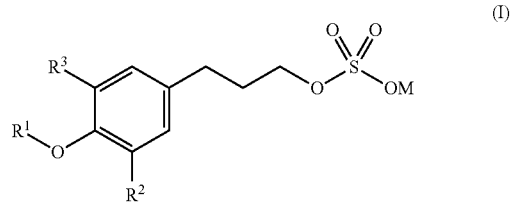

in which $R^1$ denotes a linear or branched alkyl functional group having 10 to 16 carbon atoms, $R^2$ and $R^3$, independently of one another, denote H or $H_3CO$, and M denotes hydrogen, an alkali metal or an $N^+R^4R^5R^6$ grouping, in which $R^4$, $R^5$ and $R^6$, independently of one another, denote hydrogen, an alkyl group having 1 to 6 carbon atoms or a hydroxyalkyl group having 2 to 6 carbon atoms,
comprising the step of sulfonating a compound of general formula (II),

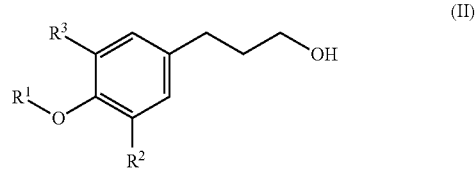

in which $R^1$ denotes a linear or branched alkyl functional group having 10 to 16 carbon atoms, $R^2$ and $R^3$, independently of one another, denote H or $H_3CO$, with a sulfating agent,
and neutralization by way of subsequent reaction with MOH, wherein M denotes an alkali metal or an $N^+R^4R^5R^6$ grouping, in which $R^4$, $R^5$ and $R^6$, independently of one another, denote hydrogen, an alkyl group having 1 to 6 carbon atoms or a hydroxyalkyl group having 2 to 6 carbon atoms.

12. The method according to claim 3, for producing a compound of general formula (II),

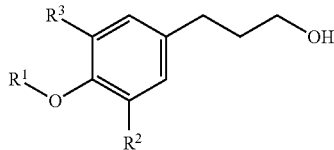
(II)

in which $R^1$ denotes a linear or branched alkyl functional group having 10 to 16 carbon atoms, $R^2$ and $R^3$, independently of one another, denote H or $H_3CO$,
comprising the step of reacting a compound of general formula (III),

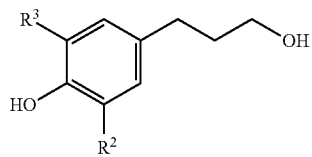
(III)

in which $R^2$ and $R^3$, independently of one another, are H or $H_3CO$,
with a compound $R^1$-Hal, in which $R^1$ denotes a linear or branched alkyl functional group having 10 to 16 carbon atoms, and Hal denotes chlorine, bromine, iodine or mixtures thereof under alkaline conditions.

13. The method according to claim 3, for producing a compound of general formula (II),

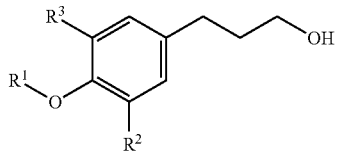
(II)

in which $R^1$ denotes a linear or branched alkyl functional group having 6 to 20 carbon atoms, $R^2$ and $R^3$, independently of one another, denote H or $H_3CO$,
comprising the step of reacting a compound of general formula (III),

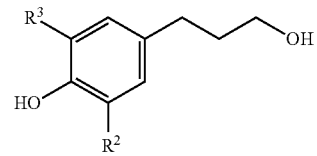
(III)

in which $R^2$ and $R^3$, independently of one another, are H or $H_3CO$,
with a compound $R^1$-Hal, in which $R^1$ denotes a linear or branched alkyl functional group having 6 to 20 carbon atoms, and Hal denotes bromine under alkaline conditions.

14. The washing or cleaning agent according to claim 4, comprising an anionic surfactant of general formula (I),

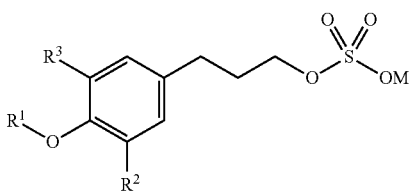
(I)

in which $R^1$ denotes a linear or branched alkyl functional group having 10 to 16 carbon atoms, $R^2$ and $R^3$, independently of one another, denote H or $H_3CO$, and M denotes hydrogen, an alkali metal or an $N^+R^4R^5R^6$ grouping, in which $R^4$, $R^5$ and $R^6$, independently of one another, denote hydrogen, an alkyl group having 1 to 6 carbon atoms or a hydroxyalkyl group having 2 to 6 carbon atoms.

15. The washing or cleaning agent according to claim 5, characterized by comprising 3 wt. % to 85 wt. % of the surfactant of general formula (I).

16. The washing or cleaning agent according to claim 6, characterized by additionally comprising 2 wt. % to 85 wt. %, of a further surfactant.

17. The washing or cleaning agent according to claim 7, characterized by being particulate and comprising builders in the range of 1 wt. % to 60 wt. %.

18. The washing or cleaning agent according to claim 8, characterized by being liquid and comprising 10 wt. % to 85 wt. %, water, water-miscible solvent or a mixture of water and water-miscible solvent.

* * * * *